(12) United States Patent
Marlow

(10) Patent No.: US 11,020,233 B2
(45) Date of Patent: Jun. 1, 2021

(54) TAPERED FIXATION DEVICE FOR A KNEE REPLACEMENT

(71) Applicant: Aaron Marlow, Suffolk, VA (US)

(72) Inventor: Aaron Marlow, Suffolk, VA (US)

(*) Notice: Subject to any disclaimer, the term of this patent is extended or adjusted under 35 U.S.C. 154(b) by 0 days.

(21) Appl. No.: 16/637,458

(22) PCT Filed: Jul. 16, 2018

(86) PCT No.: PCT/US2018/042248
§ 371 (c)(1),
(2) Date: Feb. 7, 2020

(87) PCT Pub. No.: WO2019/018266
PCT Pub. Date: Jan. 24, 2019

(65) Prior Publication Data
US 2020/0246152 A1    Aug. 6, 2020

Related U.S. Application Data

(60) Provisional application No. 62/533,251, filed on Jul. 17, 2017.

(51) Int. Cl.
*A61F 2/38* (2006.01)
*A61F 2/30* (2006.01)

(52) U.S. Cl.
CPC ............ *A61F 2/38* (2013.01); *A61F 2/30734* (2013.01); *A61F 2/30771* (2013.01);
(Continued)

(58) Field of Classification Search
CPC ...... A61F 2/389; A61F 2/3868; A61F 2/3859; A61F 2/30734; A61F 2002/2825; A61F 2/38
See application file for complete search history.

(56) References Cited

U.S. PATENT DOCUMENTS

| 4,314,381 A | | 2/1982 | Koeneman |
| 5,609,645 A | * | 3/1997 | Vinciguerra ........ A61F 2/30734 |
| | | | 623/20.28 |

(Continued)

FOREIGN PATENT DOCUMENTS

| EP | 0 420 460 | 4/1991 |
| EP | 0 765 644 | 4/1997 |

OTHER PUBLICATIONS

International Search Report and Written Opinion of the ISA for PCT/US2018/042248 dated Oct. 15, 2018, 16 pages.
(Continued)

*Primary Examiner* — Jason-Dennis N Stewart
(74) *Attorney, Agent, or Firm* — Nixon & Vanderhye P.C.

(57) ABSTRACT

A fixation device for a knee replacement. The fixation device includes a stem configured to be fixedly attached to one of a tibial component of the knee replacement and a femoral component of the knee replacement. The stem has a continuously tapered outer surface and has a distal end that is distal to said one of the tibial component and the femoral component. A tapered projection is positioned on the continuously tapered outer surface and is tapered in the same direction as the continuously tapered outer surface. The stem and the tapered projection are configured so that the continuously tapered outer surface and the tapered projection engage a patient's bone when the stem is inserted into a bone canal within the patient's bone. In addition, the continuously tapered outer surface of the stem at the distal end of the stem and the tapered projection are configured to mechanically fix the knee replacement to the patient's bone by being wedged within the bone canal.

38 Claims, 15 Drawing Sheets

(52) U.S. Cl.
CPC ............ *A61F 2/389* (2013.01); *A61F 2/3859* (2013.01); *A61F 2002/3093* (2013.01); *A61F 2002/30113* (2013.01); *A61F 2002/30158* (2013.01); *A61F 2002/30332* (2013.01); *A61F 2002/30433* (2013.01); *A61F 2002/30507* (2013.01); *A61F 2002/30593* (2013.01); *A61F 2002/30616* (2013.01); *A61F 2002/30736* (2013.01); *A61F 2002/30738* (2013.01); *A61F 2002/30879* (2013.01); *A61F 2002/30884* (2013.01); *A61F 2002/30889* (2013.01); *A61F 2002/30891* (2013.01); *A61F 2002/30932* (2013.01); *A61F 2310/00958* (2013.01)

(56) References Cited

U.S. PATENT DOCUMENTS

| | | | |
|---|---|---|---|
| 5,935,173 A * | 8/1999 | Roger | A61F 2/3868 623/20.31 |
| 6,102,957 A | 8/2000 | Noble et al. | |
| 7,799,085 B2 * | 9/2010 | Goodfried | A61F 2/30734 623/20.15 |
| 7,806,936 B2 | 10/2010 | Wright | |
| 7,892,290 B2 | 2/2011 | Bergin et al. | |
| 9,301,846 B2 | 4/2016 | Landon | |
| 9,381,090 B2 | 7/2016 | Wentorf et al. | |
| 9,532,879 B2 | 1/2017 | Lieberman et al. | |
| 9,668,889 B2 | 6/2017 | Holt et al. | |
| 2008/0091271 A1 | 4/2008 | Bonitati et al. | |
| 2012/0209391 A1 | 8/2012 | Cipolletti et al. | |
| 2014/0081409 A1 * | 3/2014 | James | A61F 2/30734 623/20.15 |
| 2014/0277551 A1 | 9/2014 | Lindsay et al. | |

OTHER PUBLICATIONS

"Biomet OSS: Orthopaedic Salvage System" Biomet Orthopedics, 2014, 24 pages.

"Sigma Revision Knee and M.B.T. Revision Tray" DePuy Synthes, Aug. 2016, 84 pages.

* cited by examiner

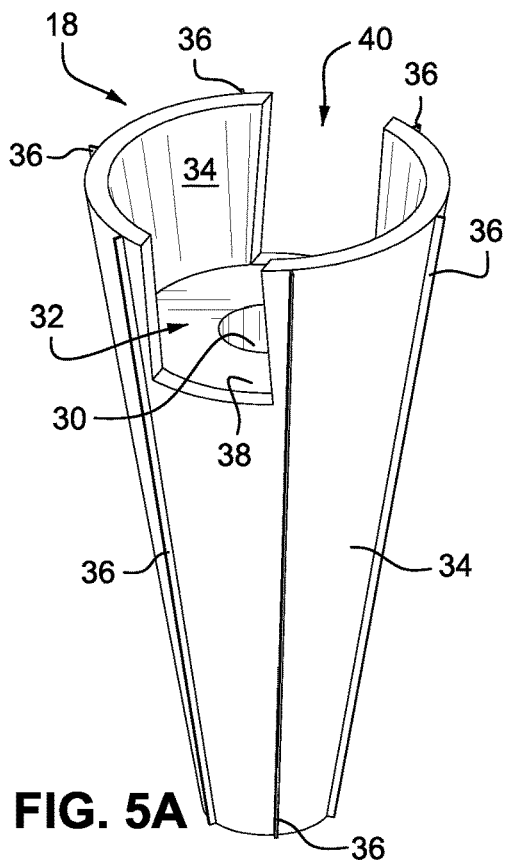 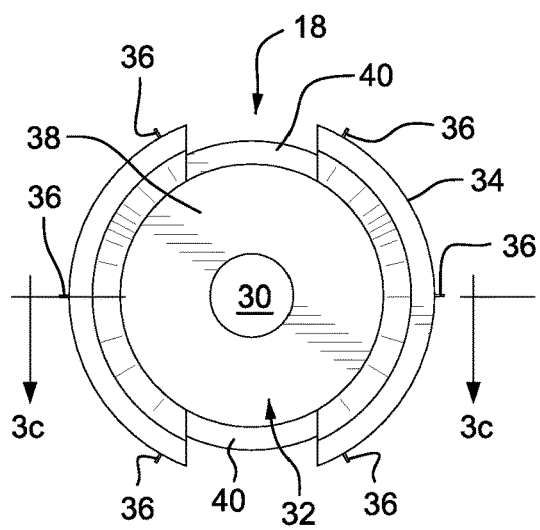 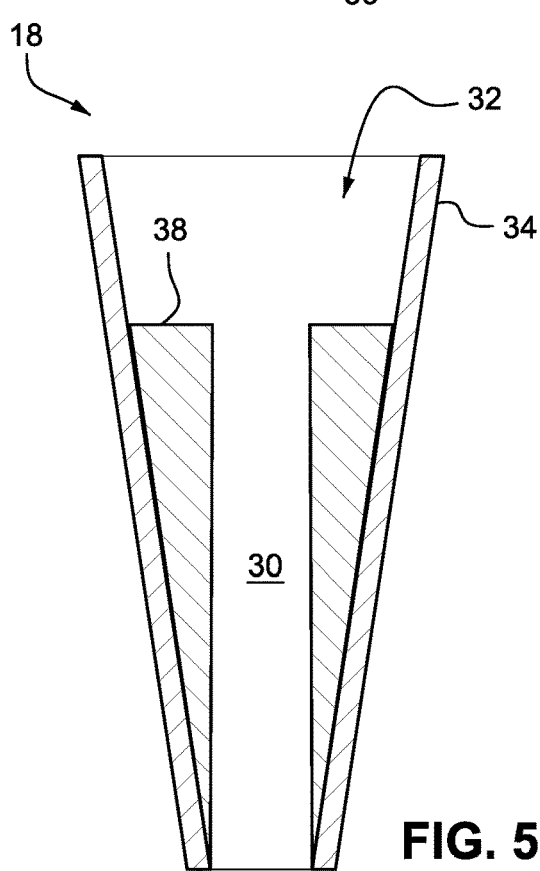 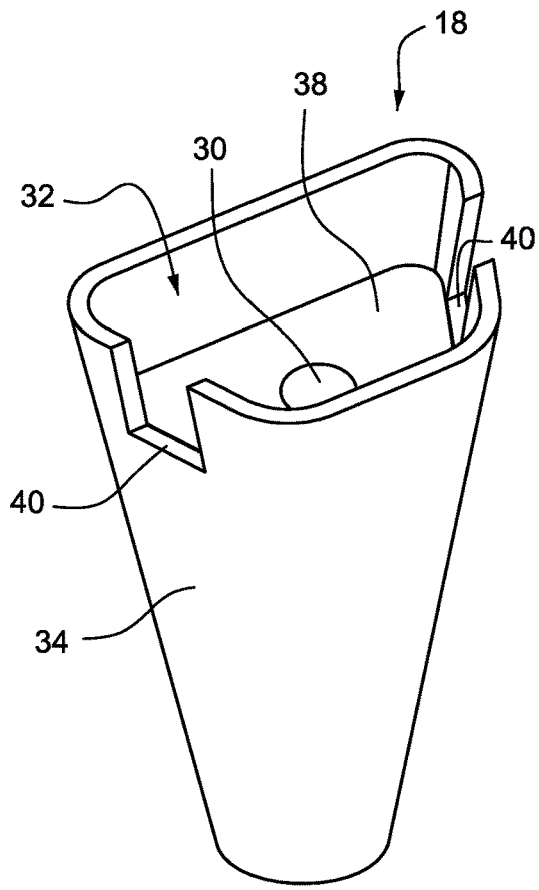
FIG. 5A
FIG. 5B
FIG. 5C
FIG. 5D

TAPERED FIXATION DEVICE FOR A KNEE REPLACEMENT

This application is the U.S. national phase of International Application No. PCT/US2018/042248 filed Jul. 16, 2018 which designated the U.S. and claims benefit to U.S. Provisional Application 62/533,251 filed Jul. 17, 2017, the entire contents of each of which are hereby incorporated by reference.

FIELD OF THE TECHNOLOGY

The subject matter disclosed herein relates to a prosthetic knee replacement and more particularly to a tapered fixation device for securing the prosthetic knee replacement to a patient's bones.

BACKGROUND

Many knee replacement surgeries are performed annually. Typical knee replacements include a femoral component that is fixed to the patient's femur. Knee replacements also include a tibial component that is fixed to the patient's tibia. A bearing insert is sandwiched between the femoral component and the tibial component and acts a replacement for the patient's cartilage. Most knee replacements are glued to the patient's bones with bone cement. Some knee replacements are simply press fit in place without cement. Either way, most knee replacements last 10-15 years, while some fail earlier for various reasons.

When a knee replacement fails, it must be fully revised. Over the life of a knee replacement, the patient's bone tissue can deteriorate resulting in bone loss. As such, when knee replacements are revised, they typically need additional mechanical fixation to compensate for the bone loss. This additional mechanical fixation takes the form of a stem that extends from the tibial component (or the femoral component) into the patient's bone canal.

Conventional stems are cylindrical. However, bone canals are rarely cylindrical. In addition, the portions of the bone canals that engage the cylindrical stems are typically tapered. Such a configuration allows for voids between the walls of the bone canal and the cylindrical stem, which allow the cylindrical stem to move or shift within the bone canal. Such movement or shifting can impede the cylindrical stem's ability to provide sufficient mechanical fixation, which in turn, can compromise the life of the revision knee replacement and can even cause pain to the patient.

Several solutions have been presented to compensate for the suboptimal fit of the cylindrical stem within the patient's bone canal. One solution uses bone cement to fill the voids between the cylindrical stem and the wall of the bone canal. However, all knee replacements (including revision knee replacement) have a limited life expectancy. In the event of knee replacement failure, the bone cement makes it more difficult to remove the previous knee replacement and contributes to even more bone loss with subsequent decreased structural support from the bone.

Another solution uses a hollow metallic support cone. The revision stem extends through the metallic support cone but is not affixed to the metallic support cone. Also, the metallic support cone is not fixed to the tibial component. This configuration allows for movement of the cylindrical stem relative to the metallic support cone, which in turn allows for movement of the revision stem relative to the bone canal. Cement is often used to fill this void. In addition, due to the unique nature of revision knee surgery, this system requires a large inventory. For example, upwards of 50 stems and 10 cones are required to ensure that the correct components are matched to the patient's specific geometry and fixation needs.

Another solution extends the length of the cylindrical stem so that it projects further into the patient's bone canal. Although this configuration may provide more support for the knee replacement, the extra length projecting deeper into the patient's bone canal can cause pain.

Yet another solution uses a stepped metallic sleeve that is fixed to the cylindrical stem. This configuration is not able to "wedge" into the patient's bone canal due to its "stepped" structure, thereby limiting its ability to support the prosthesis. In addition, the metallic sleeve is not versatile and is compatible with only one knee replacement system. Furthermore, due to the unique nature of revision knee surgery, this system requires a large inventory. For example, upwards of 50 stems and 10 sleeves are required to ensure that the correct components are matched to the patient's specific geometry and fixation needs.

BRIEF SUMMARY

Aspects of the tapered stem and the associated knee replacement described herein provide solutions to one or more problems or disadvantages associated with the prior art.

In one aspect of the technology, a fixation device for a knee replacement may be provided. The knee replacement may have a tibial component and a femoral component. The fixation device may have a stem configured to be fixedly attached to one of the tibial component and the femoral component. The stem may have a continuously and/or variably tapered outer surface and may have a distal end that is distal to said one of the tibial component and the femoral component. The stem may be configured so that the continuously tapered outer surface engages a patient's bone when the stem is inserted into a bone canal within the patient's bone. In addition, the continuously tapered outer surface of the stem at the distal end may be configured to mechanically fix the knee replacement to the patient's bone by being wedged within the bone canal.

In another aspect of the technology, a fixation device for a knee replacement may be provided. The knee replacement may have a tibial component configured to be secured to a tibia of a patient and a femoral component configured to be secured to a femur of a patient. The fixation device may include a stem configured to be wedged into one of the patient's bone canals. The stem may have an outer surface and at least a portion of the outer surface may be continuously tapered. In addition, the outer surface of the stem may be shaped to substantially match a shape of the patient's bone canal so that a furthest extension of the stem away from the knee replacement wedges in the patient's bone canal when the stem is inserted into the patient's bone canal.

In yet another aspect of the technology, a fixation device may be provided for a knee replacement. The knee replacement may have a tibial component and a femoral component. The fixation device may include a tapered stem configured to be attached to one of the tibial component and the femoral component. The fixation device may also include at least one projection on an outer surface of the tapered stem. The at least one projection may be configured to resist a rotational movement of the tapered stem when the tapered stem is inserted into a patient's bone canal. The fixation device may further include a fixation bolt configured to secure the tapered stem to the tibial component or the femoral component. The tapered stem may have a continuously tapered outer surface configured to be wedged within the patient's bone canal.

The fixation device with the tapered stem may provide the additional stability and fixation needed by patients with compromised bone stock. The "wedging" effect of the tapered design may increase bone loading, which in turn, may provide superior mechanical fixation without the need for cement in the bone canal. In addition, the use of projections (that may be in the form of splines or ribs) on the tapered stem may enhance rotational stability. It is contemplated that in addition to (or alternative to) the projections, the surface of the tapered stem may be roughened, polished or coated to add texture to the surface of the tapered stem to further enhance rotational stability. The coating may include (but may not be limited to) hydroxyapatite or similar elements. For the coating, any biocompatible surface finish may be applied. Providing a textured surface on the tapered stem in combination with the lack of cement may prevent bony ingrowth (or ongrowth) and make it easier to remove the knee replacement while also minimizing bone loss.

The additional stability and fixation may increase the longevity of the knee implant. Also, the design of the fixation device with the tapered stem is can be rigidly affixed to "off-the-shelf" knee implants. Accordingly, the configuration of the tapered stem may simplify installation of the knee replacement and reduce surgery times. It should be understood that the fixation device with the tapered stem may be used in most revision knee replacement surgeries or difficult primary surgeries.

In addition, the tapered design may reduce the amount of inventory needed to ensure that the correct components are matched to the patient's specific geometry and fixation needs. For example, the inventory may be reduced to no more than ten stems of different dimensions. This may save manufacturing and carrying costs.

In yet another aspect of the technology, a fixation device may be provided for a knee replacement. The fixation device may include a stem configured to be fixedly attached to one of a tibial component of the knee replacement and a femoral component of the knee replacement. The stem may have a continuously tapered outer surface and has a distal end that is distal to said one of the tibial component and the femoral component. A tapered projection may be positioned on the continuously tapered outer surface and may be tapered in the same direction as the continuously tapered outer surface. The stem and the tapered projection may be configured so that the continuously tapered outer surface and the tapered projection engage a patient's bone when the stem is inserted into a bone canal within the patient's bone. In addition, the continuously tapered outer surface of the stem at the distal end of the stem and the tapered projection may be configured to mechanically fix the knee replacement to the patient's bone by being wedged within the bone canal.

The patient's bone canal may become enlarged due to degradation of the bone or other issues. The tapered projection on the outer surface of the stem may provide additional structure that may be useful to fill the enlarged bone canal.

In yet another aspect of the technology, a knee replacement device may include a tibial component configured to be secured to the patient's tibia, a femoral component configured to be secured to the patient's femur, and a bearing insert sandwiched between the tibial component and the femoral component. A fixation device may be formed unitarily with one of the tibial component or the femoral component.

The fixation device may include a stem configured to be wedged into the patient's bone canal. The stem may include an outer surface and at least a portion of the outer surface may be continuously tapered. The outer surface of stem may be shaped to substantially match a shape of the bone canal so that a furthest extension of the stem away from the bearing insert wedges in the bone canal when the stem is inserted into the bone canal.

BRIEF DESCRIPTION OF THE DRAWINGS

FIG. 5A is a perspective view of an exemplary stem for use in the knee replacement of FIG. 1.

FIG. 5B is a top view of the stem of FIG. 5A.

FIG. 5C is a sectional view of the stem of FIG. 5A.

FIG. 5D is a perspective view of another exemplary stem.

DETAILED DESCRIPTION

It should be understood that the various numbers in the figures represent like components through the several views.

Figure 1:
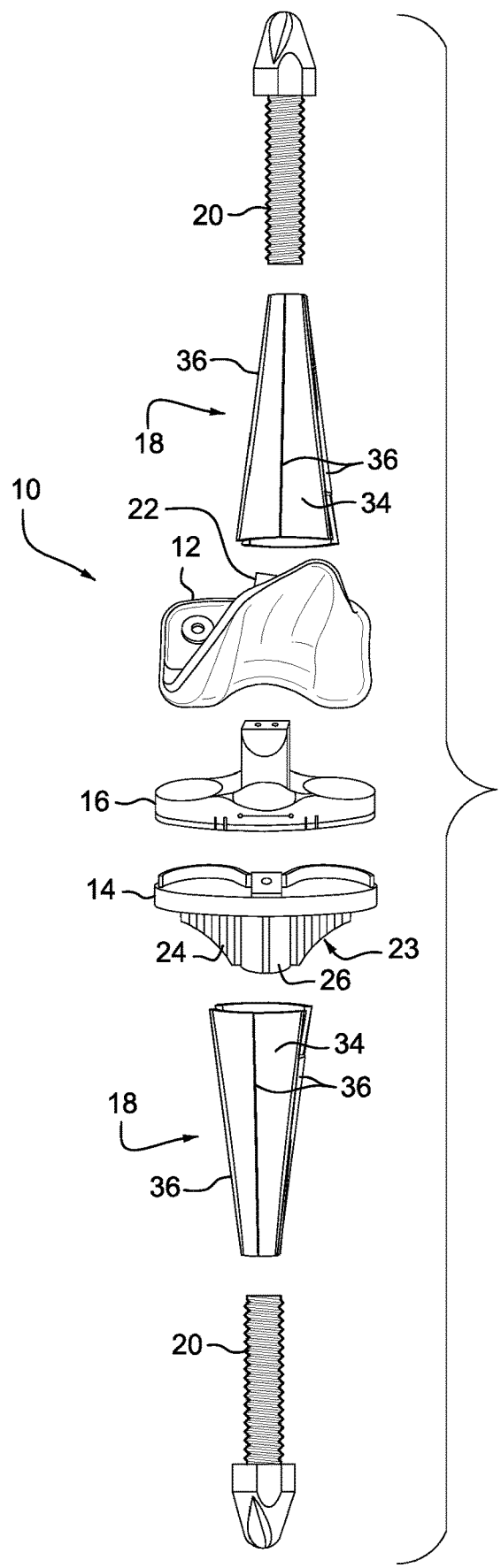
FIG. 1 is an exploded view of a knee replacement.
Figure 2:
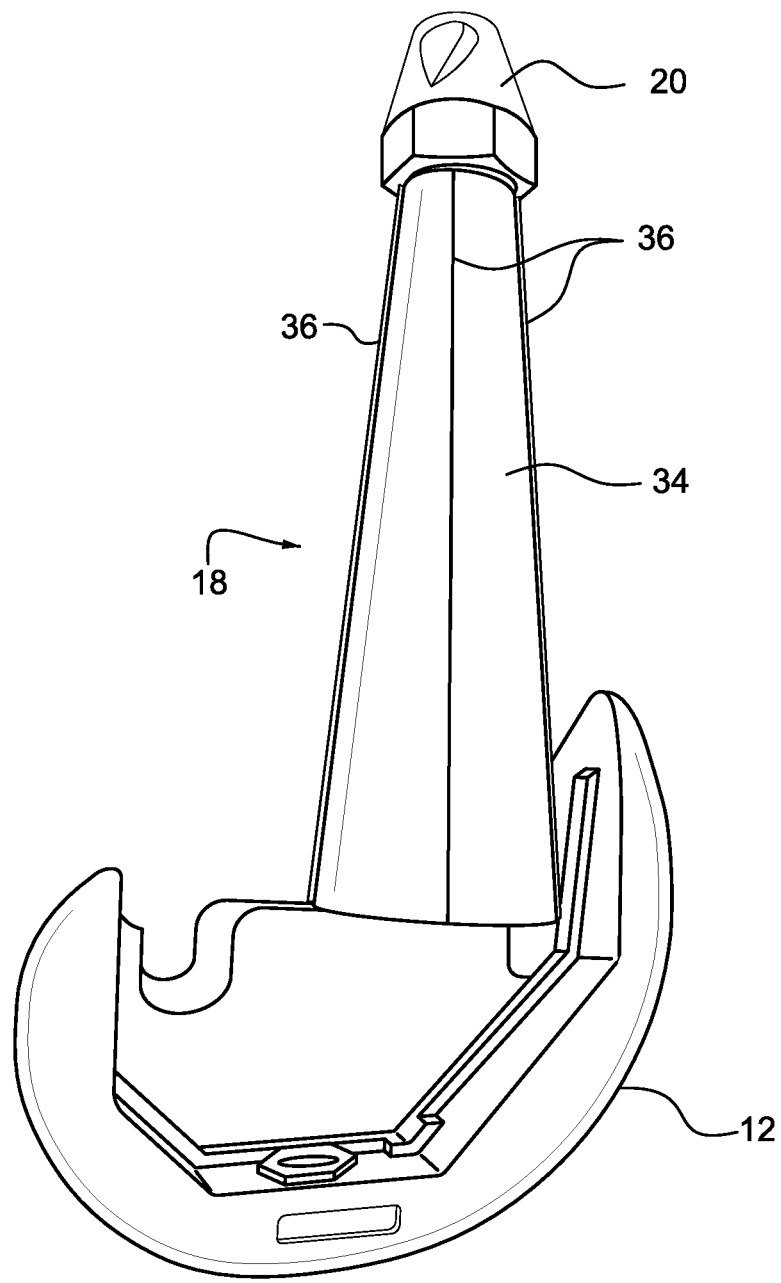
FIG. 2 is a perspective view of the knee replacement of FIG. 1 without the tibial component but with a tapered stem attached.
Figure 3:
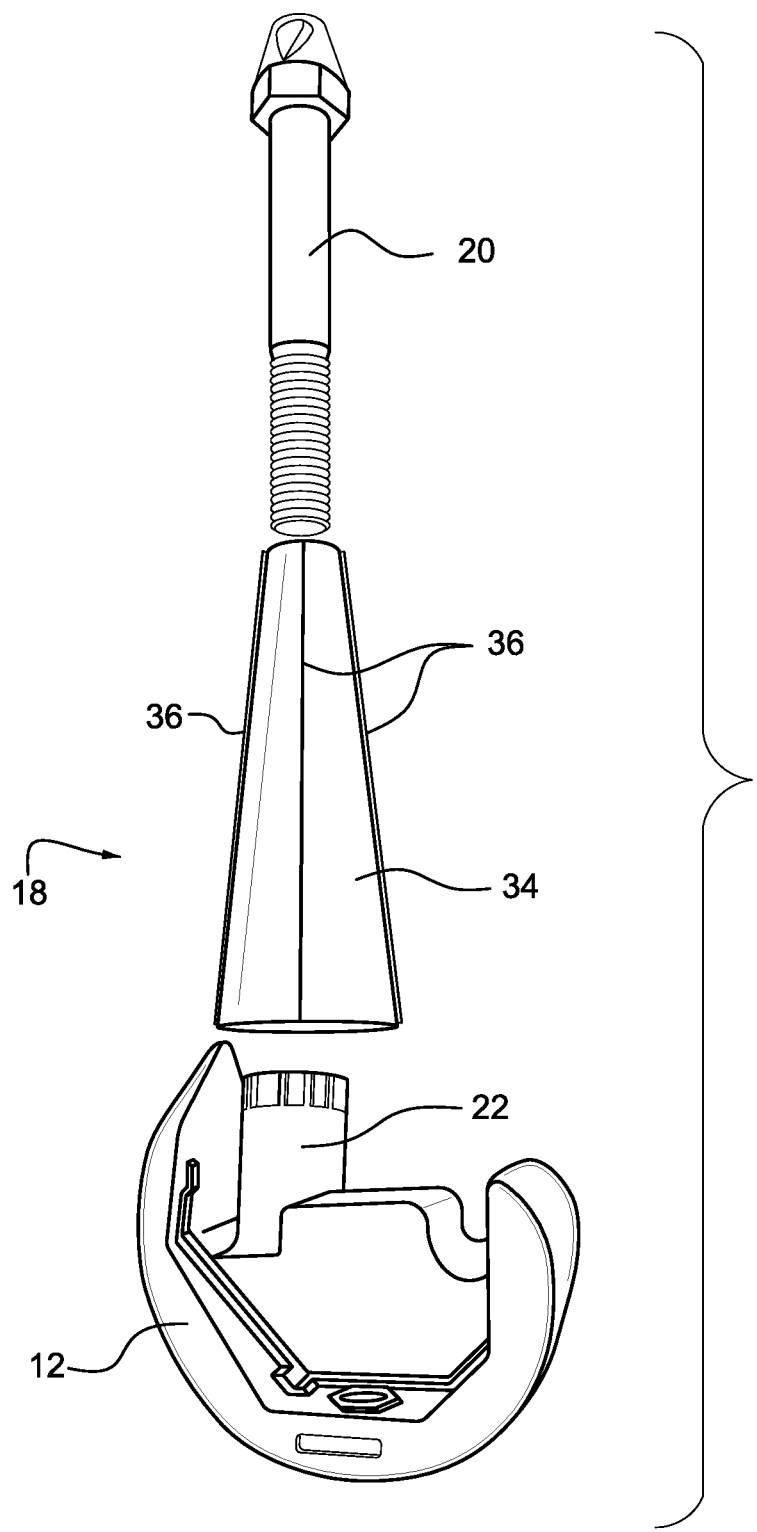
FIG. 3 is an exploded view of the femoral component with the tapered stem.
Figure 4:
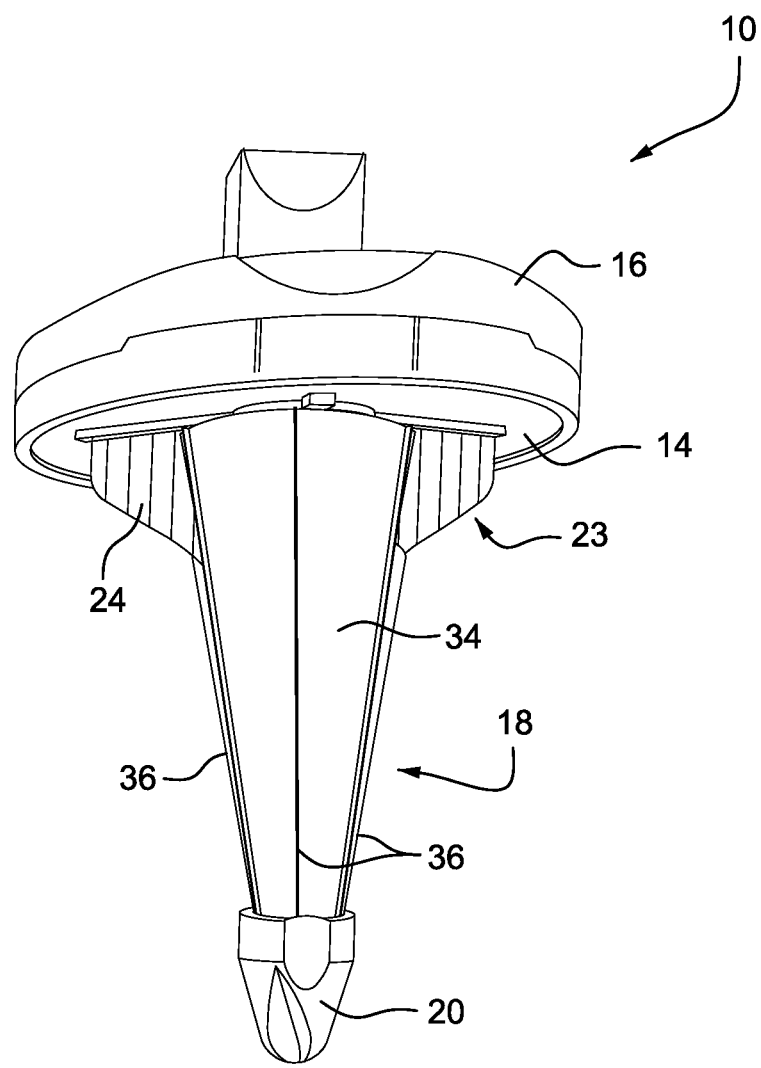
FIG. 4 is a perspective view of the knee replacement of FIG. 1 without the femoral component but with a tapered stem attached.

FIG. 1 illustrates a knee replacement 10. The knee replacement 10 may be used as a primary knee replacement that forms a prosthetic replacement for a patient's knee. The knee replacement 10 may alternatively be used as a revision knee replacement for replacing a failed primary knee replacement or a failed revision knee replacement or difficult primary replacement. The knee replacement 10 may include a femoral component 12, a tibial component 14, a bearing insert 16, one or two stems 18 and corresponding fixation bolts 20.

The femoral component 12 may form an upper portion of the knee replacement 10 and may be secured to a lower end of the patient's femur (not shown). In addition, the femoral component may be made of biocompatible material such as, for example, biocompatible metal. In addition, an upper portion of the femoral component 12 may include a stem engagement portion 22 that may engage a surface of the stem 18 and receive the bolt 20. It is contemplated that the stem engagement portion 22 and/or other parts of the femoral component 12 may interact with the stem 18 to resist rotational movement of the stem 18 relative to the femoral component 12. It is further contemplated that the stem engagement portion 22 may be in the form of a cylinder or other hollow shape or tapered or solid shape. The cylinder may be received inside the stem 18, and the bolt 20 may be received inside the hollow portion of the stem engagement portion 22. It is contemplated that the hollow portion of the stem engagement portion 22 may be threaded to match a threading on the fixation bolt 20. The hollow portion of the stem engagement portion 22 may include other features instead of threading that may mechanically fix the fixation bolt 20 and the stem 18 to the femoral component 12. The hollow portion of the stem engagement portion 22 and the fixation bolt 20 may work together to fixedly secure the stem 18 to the top side of the femoral component 12 and resist any movement of the stem 18 relative to the femoral component 12. The head of the fixation bolt 20 may vary in shape, size, length, surface finish and material. In addition, the head of the fixation bolt 20 may include a tuning fork/clothes peg end or other modified end to decrease terminal stiffness.

The tibial component 14 may form part of a lower portion of the knee replacement 10 and may be secured to an upper end of the patient's tibia (not shown). The tibial component 14 may also be made of biocompatible material such as, for example, biocompatible metal. In addition, a lower portion of the tibial component 14 may include a stem connection portion 23. The stem 18 may connect to the tibial component 14 at the stem connection portion 23.

The stem connection portion 23 may be the portion of the tibial component 14 that connects to the stem 18. The stem connection portion 23 may include an engagement portion 24 and a bore 26. The stem engagement portion 24 may engage a surface of the stem 18. It is contemplated that, the stem engagement portion 24 may interact with the stem 18 to resist rotational movement of the stem 18 relative to the tibial component 14. At least part of the engagement portion 24 may be rib-shaped (or any other shape) and may provide structural support to the rest of the tibial component 14.

The bore 26 may receive the fixation bolt 20 to secure the stem 18 to the tibial component. It is contemplated that the bore 26 may be threaded to match a threading on the fixation bolt 20. The bore 26 may include other features instead of threading that may mechanically fix the fixation bolt 20 and the stem 18 to the tibial component 14. The bore 26 and the fixation bolt 20 may work together to fixedly secure the stem 18 to the underside of the tibial component 14 and resist any movement of the stem 18 relative to the tibial component 14.

The bearing insert 16 may be positioned between the femoral component 12 and the tibial component 14 and may replace the patient's cartilage. In addition, the bearing insert 16 may be made of a biocompatible plastic. Preferably, the biocompatible plastic may be a low friction material so that the femoral component 12 may easily slide along the surface of the bearing insert 16.

The stem 18 may extend from the tibial component 14 and may further secure the knee replacement 10 to the patient's tibia by way of a bone canal inside the patient's tibia (not shown). FIGS. 1-4 illustrate one stem 18 extending from the tibial component 14 and another stem extending from the femoral component 12. It is contemplated that the knee replacement 10 may include one or two stems 18. In those configurations, the stem 18 may extend from the femoral component 12 and/or the tibial component 14.

The stem 18 may include a central bore 30, an internal receiving portion 32, an outer surface 34 and at least one projection 36. In addition, the stem 18 may be made of any biocompatible material. For example, the stem 18 may be made of biocompatible metal. It is contemplated that different components of the stem 18 may be made of different biocompatible materials. It is contemplated that the central bore 30 may also be offset as illustrated in FIGS. 10A-10D (offset bore 330).

The central bore 30 may be sized to receive the fixation bolt 20. In addition, the central bore 30 may have a cylindrical or tapered shape and may be threaded to match a threading on the fixation bolt 20. Alternatively, the walls of the central bore 30 may be smooth so that the fixation bolt 20 may simply slide through the central bore 30 rather than be screwed into the central bore 30. It is further contemplated that the central bore 30 may include other features instead of threading that may facilitate mechanically fix the fixation bolt 20 and the stem 18 to the tibial component 14.

The internal receiving portion 32 may be a recess at one end of the stem 18 that receives the engagement portion 24. The internal receiving portion 32 may include a seat 38 and gaps 40.

The central bore 30 may terminate at the seat 38. In addition, when assembled to the tibial component 14 (or the femoral component 12), the stem engagement portion 24 may abut against the seat 38 so that the bore 26 and the central bore 30 together form a continuous cavity that receives the fixation bolt 20.

The gaps 40 may be positioned to receive the stem engagement portion 24. Although illustrated as relatively wide, the gaps 40 may be narrowed to substantially match the thickness (i.e., within manufacturing tolerances) of the engagement portion 24 so that the gaps 40 cooperate with the engagement portion 24 to resist rotational movement of the stem 18 relative to the tibial component 14.

The outer surface 34 may be tapered from the internal receiving portion 32 to the opposite end of the stem 18. As can be seen in FIGS. 1-6C, the tapered shape of the outer surface 34 may be continuous. This may ensure that a tapered surface engages the patient's bone canal. Ensuring that a tapered surface engages the patient's bone canal allows the outer surface 34 to be wedged in the tapered portion of the patient's bone canal. The wedging of the outer surface 34 may be the primary way the stem 18 fixes the knee replacement 10 to the patient's bone canal.

It should be understood that the wedging of the outer surface 34 against the patient's bone canal may be facilitated by selecting a shape and/or material that provides some amount of elasticity so that the stem 18 may be "squeezed" or may be compressed when pushed into engagement with the walls of the patient's bone canal. The elasticity of the stem 18 may be closer to that of bone than conventional methods of fixation, thereby reducing implant related bone pain while reducing risks of stress shielding. It should be further understood that tapering the outer surface 34 to enable the outer surface 34 to be wedged against the walls of the patient's bone canal may substantially increase the force retaining the knee replacement 10 in place. In particular, the tapered outer surface 34 may substantially match the taper within the bone canal, which may substantially increase the surface area of the engagement zone between the stem 18 and the walls of the bone canal. For example, the engagement zone may be equivalent to the entire length of the outer surface 34 or a substantially large portion of the outer surface 34. The ultimate result of the tapered configuration may be a more spread out and increased force holding the knee replacement 10 in place due to a much greater area of interaction between the walls of the bone canal and the outer surface 34 of the stem 18. In addition, the stability of the knee replacement 10 may be increased by ensuring that at least the most distal end of the outer surface 34 (i.e., the end that is furthest from the tibial component 14 or the femoral component 12) is wedged against the walls of the bone canal. The stem 18 may also include radial steps and/or macrotexture that may convert axial forces to compression forces, thereby decreasing stress and increasing surface area.

It is contemplated that the outer surface 34 may be roughened, polished or coated to add texture to the surface 34 to provide some rotational support. For example, the surface 34 have a grit blasted finish and/or a coating that includes (but is not limited to) hydroxyapatite or similar elements or any other biocompatible material. The grit blasted finish and/or coating may prevent bony ingrowth (or ongrowth), which may facilitate easy removal of the stem 18. It is further contemplated that instead of a grit blasted finish or in addition to the grit blasted finish, other textured features may be added to the outer surface 34 to increase the surface roughness of the outer surface 34.

In addition, a cross-sectional shape of the outer surface 34 (as viewed along the axis of the stem 18) may be symmetrical (as illustrated in the drawings) or asymmetrical. The asymmetrical shape/configurations may be used when the patient's anatomy requires a relatively shifted or offset position of the baseplate 14 relative to the bony canal to provide an optimal fit of a baseplate of the tibial component 14 to the end of the bone. The cross-sectional shape of the outer surface 34 may be circular, trapezoidal or any other shape that may substantially match or compliment the cross-sectional shape of the patient's bony canal. It is contemplated that the cross-sectional shape of the outer surface 34 may vary along the axis of the stem 18. For example, the cross-sectional shape of the portion of the outer surface 34 at the internal receiving portion 32 may be trapezoidal, while the cross-sectional shape of the portion of the outer surface 34 that is at the opposite end may be circular. The transition between cross-sectional shapes may be gradual or may be sudden.

The outer surface 34 illustrated in FIGS. 1-5C and 6A-6C are conical in shape. Thus, those figures illustrate an outer surface 34 in which the cross-sectional shape is circular throughout the stem 18. FIG. 5D illustrates a trapezoidal cross-sectional shape. It should be understood that the cross-sectional shape of the outer surface 34 is not limited to the shapes illustrated in the figures.

The projections 36 may extend axially along the outer surface 34. In addition, the projections 36 may be positioned to resist rotational movement of the stem 18 relative to the patient's bone canal. It is contemplated that the projections 36 may extend the entire length of the outer surface 34 or may extend only a fraction of the length of the outer surface 34. Although each projection 36 is illustrated as being continuous, the projections 36 may be discontinuous (i.e., there may be multiple, axially aligned, distinct projections 36). It should be understood that the stem 18 may include as few as one projection 36. Additionally, the projections 36 may be arranged symmetrically (equally spaced) or asymmetrically (not equally spaced) on the outer surface 34. Although the projections 36 are shown as being axially aligned, they may have a different orientation. For example, the projections 36 may be angled relative to the central longitudinal axis of the stem 18 or may be fully radially aligned projections.

The projections 36 may be in the form of splines or ribs. The cross-sectional shapes of the projections 36 may be trapezoidal, semicircular, triangular, square or any other shape.

The fixation bolt 20 may mechanically secure the stem 18 to the tibial component 14 (or the femoral component 12). The fixation bolt 20 may be longer than the length of the stem 18 or may be shorter than the stem 18. In addition, the fixation bolt 20 may be configured so that when fully received by the bore 26 and the central bore 30, a portion of the fixation bolt 20 remains exposed to the patient's bone canal. In this configuration, the head of the fixation bolt 20 may be wider than the diameter of the central bore 30 so that the fixation bolt 20 may hold the stem 18 against the tibial component 14 (or the femoral component 12) by a compressive force.

Alternatively, the fixation bolt 20 may be configured so that when fully received by the bore 26 and the central bore 30, a head of the fixation bolt 20 is inside the stem 18. In this configuration, the stem 18 may include a second internal receiving portion (not shown) with a second seat (not shown) that abuts the head of the fixation bolt 20 when the fixation bolt 20 is fully received by the bore 26 and the central bore 30. This may allow the fixation bolt 20 to hold the stem 18 against the tibial component 14 (or the femoral component 12) by a compressive force.

Figures 6A, 6B, 6C:
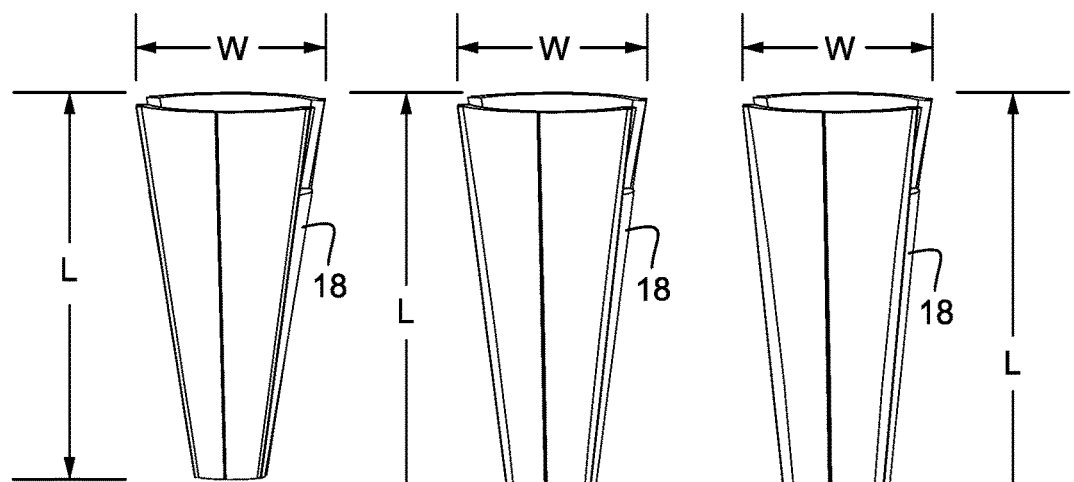
FIGS. 6A-6C are perspective views of exemplary revision stems for use in the revision knee replacement of FIG. 1.

The dimensions of the stem 18 may be selected to substantially match or compliment the dimensions of the patient's bone canal. For example, a width of the stem 18 may be in a range between approximately 2 mm to approximately 80 mm. The length of the stem 18 may be within a range of approximately 10 mm to 300 mm. For example, the stem 18 may be 70 mm. FIGS. 6A-6C illustrate stems 18 with different lengths L. As can be seen the angle of the taper of the outer surface 34 may depend on the relative widths W at the ends of the stem 18 as well as the length L of the stem 18.

Figures 7, 8:
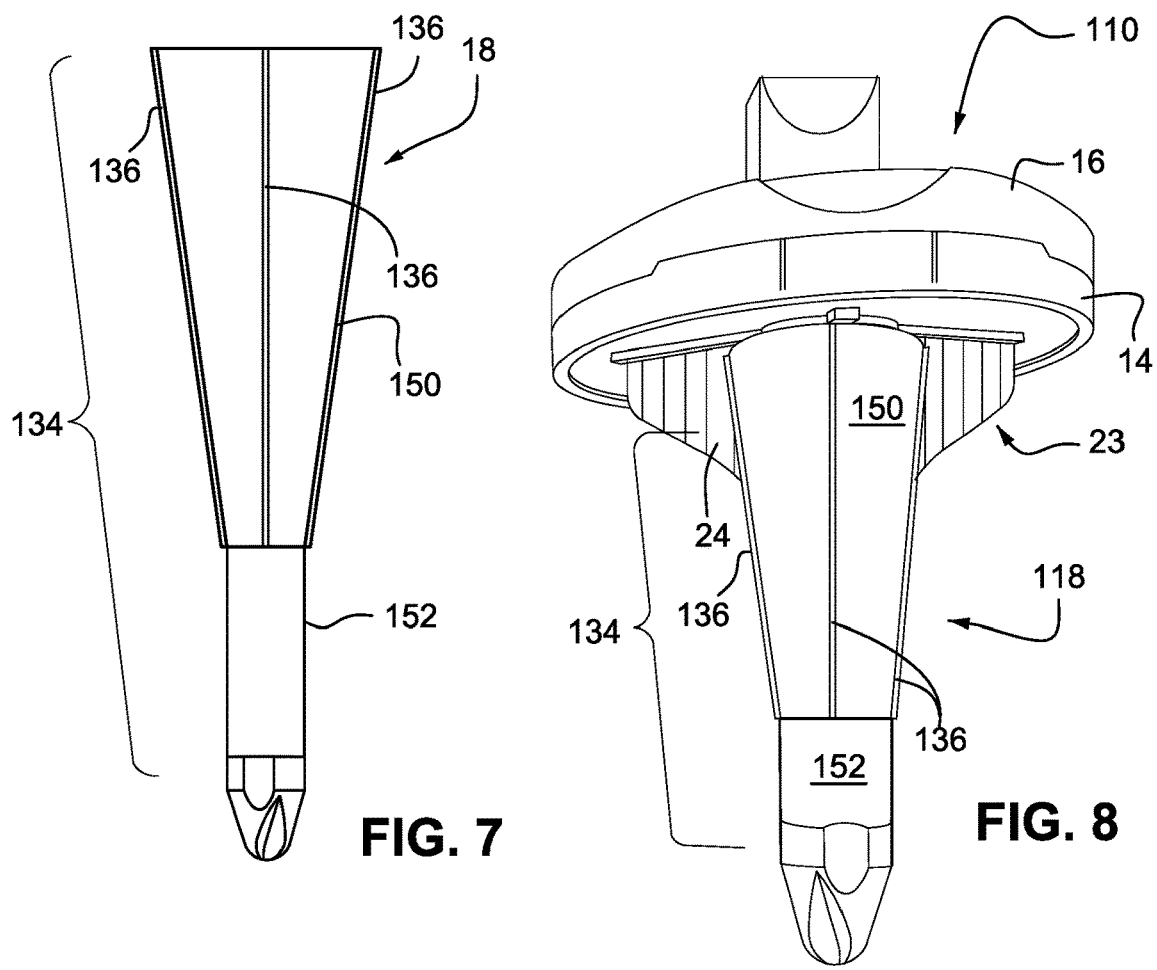
FIG. 7 is a side view of another exemplary stem.
FIG. 8 is another exemplary knee replacement without the femoral component.

FIGS. 7 and 8 illustrate a knee replacement 110 with a stem 118. All of the components of the knee replacement 110 are the same as the knee replacement 10 except for the stem 18. The only difference between the stem 18 and the stem 118 is that the entire outer surface 34 of the stem 18 is tapered. In contrast, the outer surface 134 of the stem 118 has a tapered section 150 and a non-tapered section 152.

The stem 118 may be used when the patient has severe bone loss and a more substantial mechanical fixation is needed. In such a circumstance, the stem 118 may be inserted further into the patient's bone canal than the stem 18. Typically bone canals are tapered at the end but become non-tapered in deeper sections. Thus, the tapered section 150 and the non-tapered section 152 may be designed to substantially match and/or complement the tapered and non-tapered structure of the patient's bone canal.

It is contemplated that the tapered section 150 and the non-tapered section 152 may be modular components to be assembled to each other. It is further contemplated that the tapered section 150 and the non-tapered section 152 may be formed as one piece. Also, the non-tapered section 152 may be a fixation bolt similar to the fixation bolt 20. Although the non-tapered section 152 is not tapered, the non-tapered section 152 may still vary in shape, size, length, surface finish, material and may include a tuning fork/clothes peg end or other modified end to decrease terminal stiffness.

Similar to the outer surface 34, the outer surface 134 may have a grit blasted finish to provide rotational support. The grit blasted finish may also prevent bony ingrowth, which may facilitate easy removal of the stem 118. It is further contemplated that the finish may have additional or alternative features to add texture to the outer surface 134 and to roughen the outer surface 134. The outer surface 134 may also have projections similar to the projections 36

It is contemplated that the stems 18 (or 118) may be modular components assembled to the rest of the knee replacement 10 (or 110) or may be formed as one piece with the rest of the knee replacement 10 (or 110) (i.e., the stem 18 (or 118) may be formed as one piece with the tibial component 14 or the femoral component 12). When the knee replacement 10 (or 110) includes two stems 18 (or 118), one or both stems 18 (or 118) may be formed integrally with the components of the knee replacement 10. For example, one stem 18 (or 118) may be formed integrally with the tibial component 14 with the other stem 18 (or 118) being secured to the femoral component 12 by way of the fixation bolt 20. In another example using two stems 18 (or 118), one stem 18 (or 118) may be secured to the tibial component 14, while the other stem 18 (or 118) may be formed integrally with the femoral component 12. In yet another example using two stems 18 (or 118), one stem 18 (or 118) may be formed integrally with the tibial component 14 and the other stem 18 (or 118) may be formed integrally with the femoral component 12.

Figure 9:
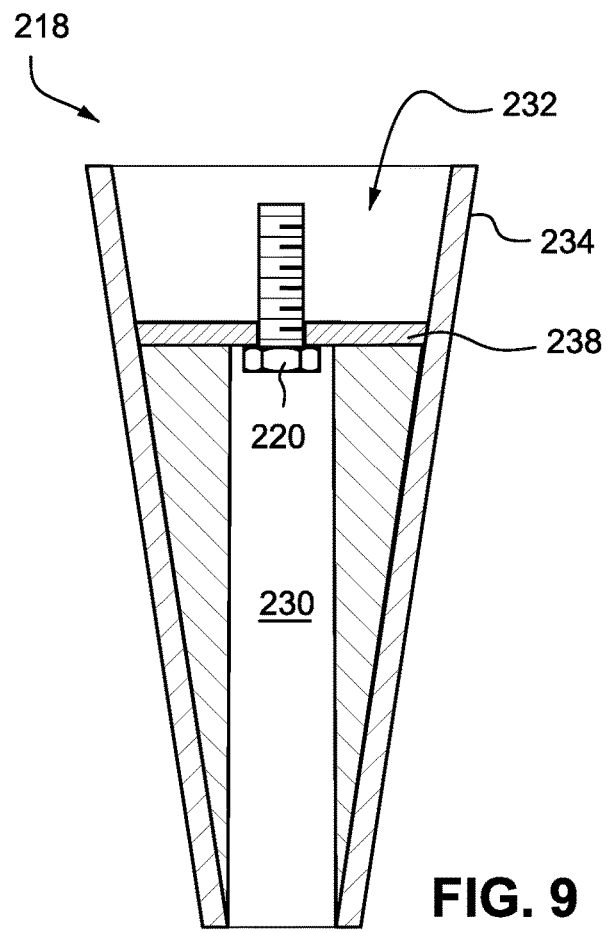
FIG. 9 is a sectional view of another exemplary stem.
Figure 10A:
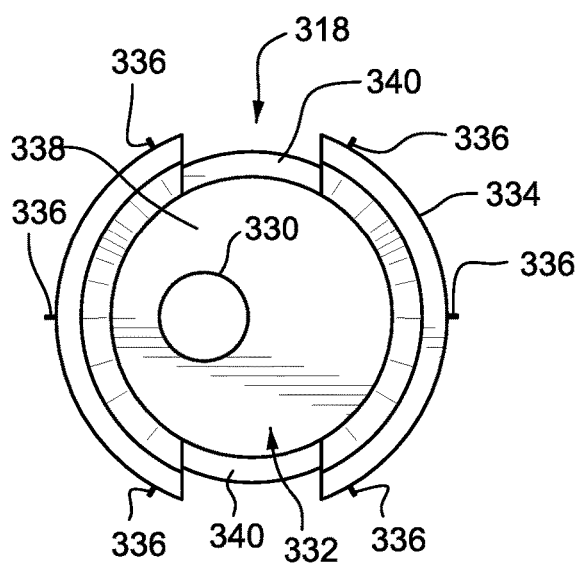
FIG. 10A is a top view of another exemplary stem.
Figure 10B:
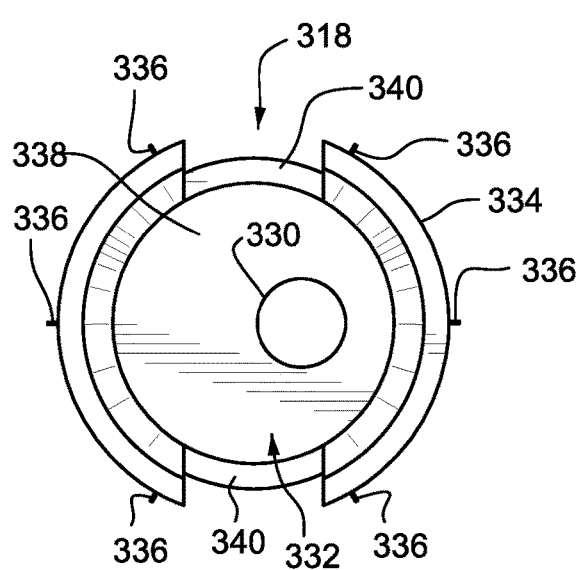
FIG. 10B is a top view of another exemplary stem.
Figure 10C:
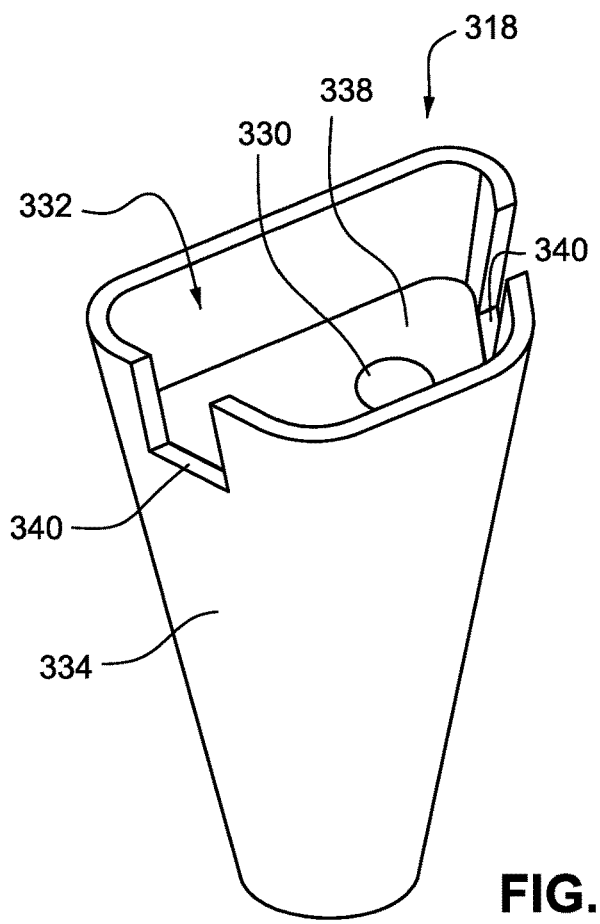
FIG. 10C is a perspective view of another exemplary stem.
Figure 10D:
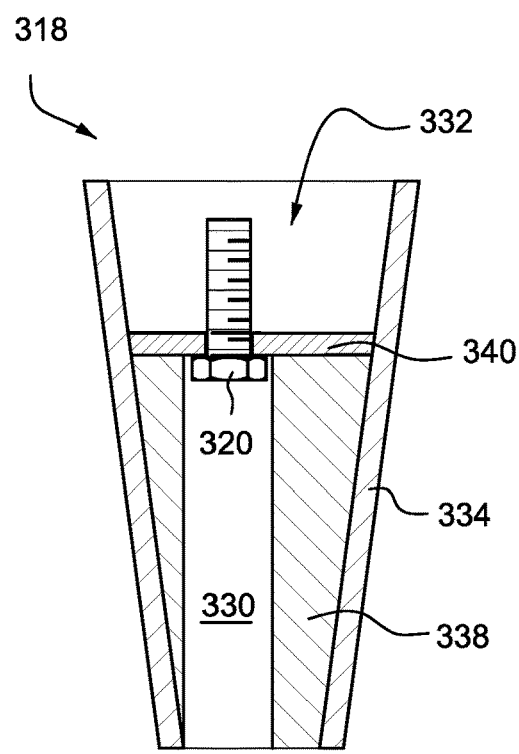
FIG. 10D is a sectional view of another exemplary stem.

FIGS. 1-8 show knee replacements that utilize a fixation bolt that may be longer than the stem to secure the stem to the tibial and/or femoral component. FIG. 9 illustrates a stem 218 that utilizes a relatively smaller fixation bolt to secure the stem 218 to the tibial and/or femoral component. The fixation bolt 220 may be shorter than the length of the stem 218. Thus, unlike the fixation bolt 20, 120 (whose head may remain outside the central bore 30, 130), the head of the fixation bolt 220 may remain within a central bore 230 of the stem 218.

The stem 218 may be similar to the stem 18. For example, the stem 218 may include an internal receiving space 232 (similar to the internal receiving space 32) that receives the stem engagement portion 22 of the femoral component 12 and/or the stem engagement portion 24 of tibial component 14. The stem 218 may have an outer surface 234 similar to the outer surface 34. For example, the outer surface 234 may be tapered and may have a surface finish and/or projections similar to the surface finish and/or projections of the outer surface 34.

The stem 218 may also include a seat 238. Similar to the seat 38, 138, the seat 238 may include an opening for receiving the fixation bolt 220. While the opening in the seat 38, 138 may have the same diameter as the central bore 30, 130, the opening in the seat 238 may have a smaller diameter than the diameter of the central bore 230. In addition, the diameter of the head of the fixation bolt 220 may be smaller than the diameter of the central bore 230 but larger than the diameter of the opening in the seat 238. This configuration may allow the fixation bolt 220 to exert a compressive force against the seat 238 when securing the stem 218 to the tibial or femoral component. In contrast, the fixation bolt 20 may exert a compressive force against a distal end of the stem 18 (the end of the stem 18 furthest from the tibial component 14 or the femoral component 12). It is contemplated that in all embodiments, the bore 30, 130, 230 may be threaded and that the force securing the stem to the tibial component 14 or the femoral component 12 may originate from the interaction between the fixation bolt and the threading inside the central bore.

Once the fixation bolt 220 is secured within the central bore 230, the distal end of the central bore 230 (the end furthest from the seat 238) may remain open or may be closed off by way of a protective covering. The protective covering may be made of any biocompatible material and may vary in shape, size, length, taper, surface finish, material. The protective covering may include a tuning fork/ clothes peg end or other modified end to decrease terminal stiffness. In addition, the central bore 230 may be filled by a filler material.

FIGS. 10A-10D illustrate a stem 318 similar to the stem 218. However, instead of a central bore centered on the longitudinal axis of the stem, the stem 318 includes an offset bore 330 that is offset from the longitudinal axis of the stem 318. The offset bore 330 may also be part of the stem 18 and the stem 118. Stems 18 and 118 may also be asymmetric.

It should be understood that the location of the offset bore 330 may be the only difference between the stem 318 and the stem 218. In particular, the stem 318 may include an internal receiving space 332 (similar to the internal receiving space 232) that receives the stem engagement portion 22 of the femoral component 12 and/or the stem engagement portion 24 of tibial component 14. The stem 318 may have an outer surface 334 similar to the outer surface 234. For example, the outer surface 334 may be tapered and may have a surface finish and/or projections 336 similar to the surface finish and/or projections of the outer surface 234.

Similar to the seat 238, the seat 338 may include an opening for receiving the fixation bolt 320 that may have a smaller diameter than the diameter of the offset bore 330. In addition, the diameter of the head of the fixation bolt 320 may be smaller than the diameter of the offset bore 330 but larger than the diameter of the opening in the seat 338. This configuration may allow the fixation bolt 320 to exert a compressive force against the seat 338 when securing the stem 318 to the tibial or femoral component. It is contemplated that the offset bore 330 may be threaded and that the force securing the stem to the tibial component 14 or the femoral component 12 may originate from the interaction between the fixation bolt 320 and the threading inside the offset bore 330.

Once the fixation bolt 320 is secured within the offset bore 330, the distal end of the offset bore 330 (the end furthest from the seat 338) may remain open or may be closed off by way of a protective covering. The protective covering may be made of any biocompatible material. In addition, the offset bore 330 may be filled by a filler material.

The stem 318 may also include gaps 340 similar to the gaps 40 of the stem 18. The gaps 340 may be positioned to receive the engagement portion 24. Although illustrated as relatively wide, the gaps 340 may be narrowed to substantially match the thickness (i.e., within manufacturing tolerances) of the engagement portion 24 so that the gaps 340 cooperate with the engagement portion 24 to resist rotational movement of the stem 318 relative to the tibial component 14.

Figures 11, 12:
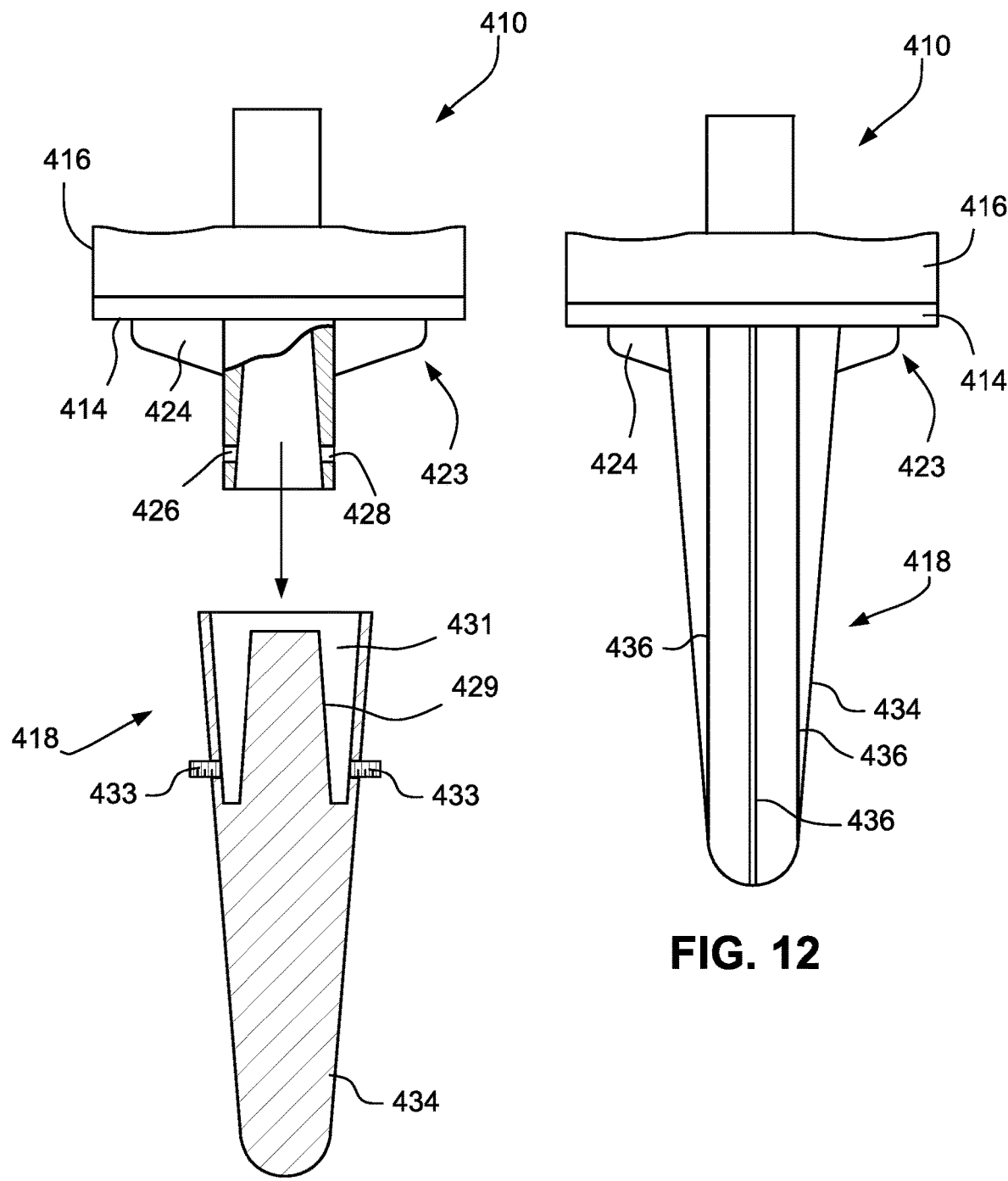
FIG. 11 is an exploded view of another exemplary knee replacement without the femoral component.
FIG. 12 is a side view of the knee replacement of FIG. 11.

FIGS. 11 and 12 illustrate another exemplary tibial component 414 of a knee replacement 410. Similar to the tibial component 14, the tibial component 414 may be secured to a bearing insert 416 (which may be similar to the bearing insert 16). The tibial component 414 may include a stem connection portion 423 that is configured to connect a stem 418 to the tibial component 414.

The stem connection portion 423 may include an engagement portion 424, a bore 426 and lateral openings 428. The engagement portion 424 may engage a surface of the stem 418. Similar to the engagement portion 24, it is contemplated that the engagement portion 424 may interact with the stem 418 to resist rotational movement of the stem 418 relative to the tibial component 414. At least part of the engagement portion 424 may be rib-shaped (or any other shape) and may provide structural support to the rest of the tibial component 414.

The bore 426 may receive an internal tapered structure 429 within an interior of the stem 418 to secure the stem 18 to the tibial component. The interior of the bore 426 may be tapered to match the tapered shape of the internal tapered structure 429. In addition, the bore 426 may be received within an internal receiving space 431 in the stem 418.

The lateral openings 428 may be sized and located to receive the set screws 433 in the side of the stem 418. When the bore 426 is received within the internal receiving space 431, the lateral openings 428 align with the set screws 433 and receive the set screws 433 to secure the stem 418 to the stem connection portion 423. The bore 426, the lateral openings 428, the internal tapered structure 429 and the set screws 433 may work together to fixedly secure the stem 418 to the underside of the tibial component 414 and resist any movement of the stem 418 relative to the tibial component 414.

It is also contemplated that the lateral openings 428 may be replaced with biased projections (not shown) that are biased in a radially outward direction. The set screws 433 may be replaced with openings or indentations (not shown) that may receive the biased projections.

The stem 418 may include an outer surface 434 similar to the outer surface 34. For example, the outer surface 434 may be tapered and may have a surface finish and/or projections 436 similar to the surface finish and/or projections of the outer surface 34.

Figure 13:
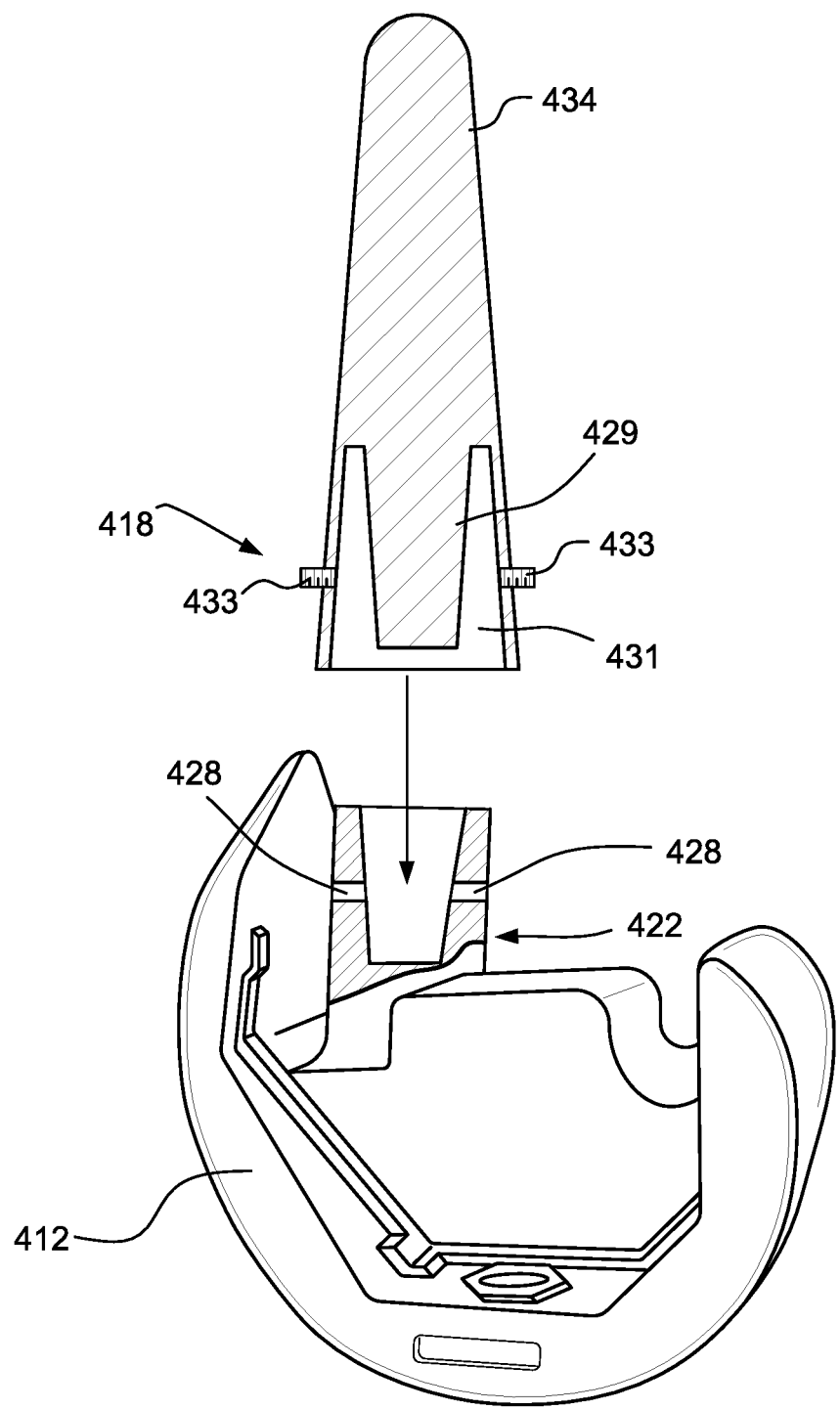
FIG. 13 is an exploded view of another exemplary knee replacement without the tibial component.

FIG. 13 shows how the stem 418 may be attached to an exemplary femoral component 412 of the knee replacement 410. Similar to the femoral component 12, an upper portion of the femoral component 412 may include an engagement portion 422 that connects the femoral component 412 to the stem 418.

Similar to the connection portion 423, the stem engagement portion 422 may include the bore 426 and the lateral openings 428. Thus, the stem 418 may connect to the femoral component 412 in a similar way as the stem 418 connects to the tibial component 414.

It is also contemplated that the lateral openings 428 may be replaced with biased projections (not shown) that are biased in a radially outward direction. The set screws 433 may be replaced with openings or indentations (not shown) that may receive the biased projections.

Figure 14A:
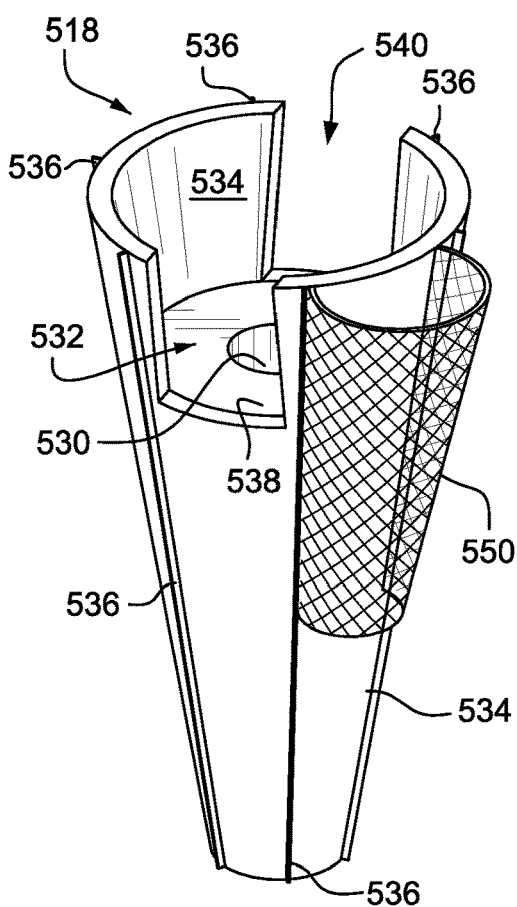
FIG. 14A is a perspective view of an exemplary stem with a tapered projection.
Figure 14B:
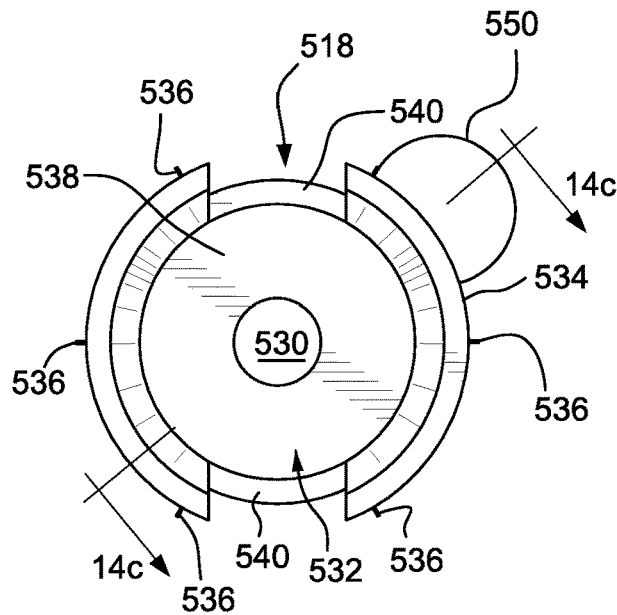
FIG. 14B is a top view of the stem of FIG. 14A.
Figure 14C:
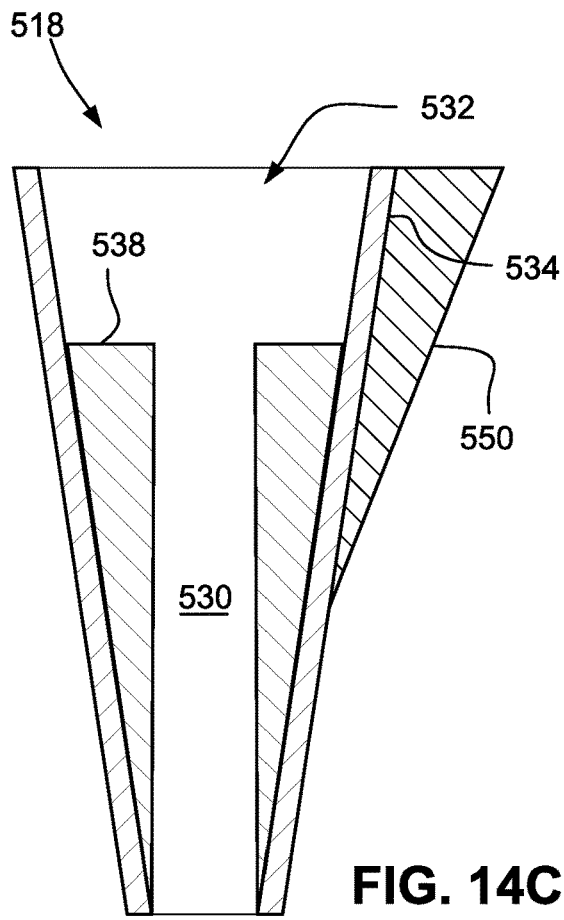
FIG. 14C is a side view of an exemplary stem with a tapered projection.
Figure 15A:
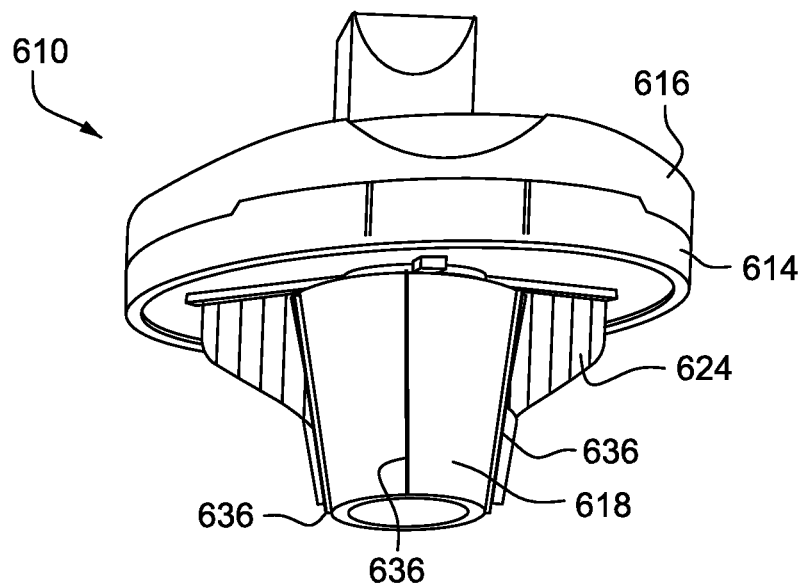
FIGS. 15A-18B illustrate exemplary non-modular knee replacement devices.
Figure 15B:
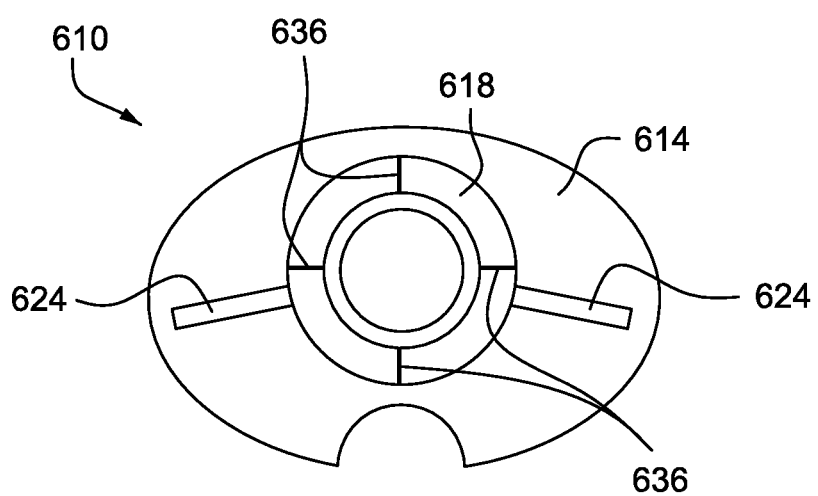
Figure 16A:
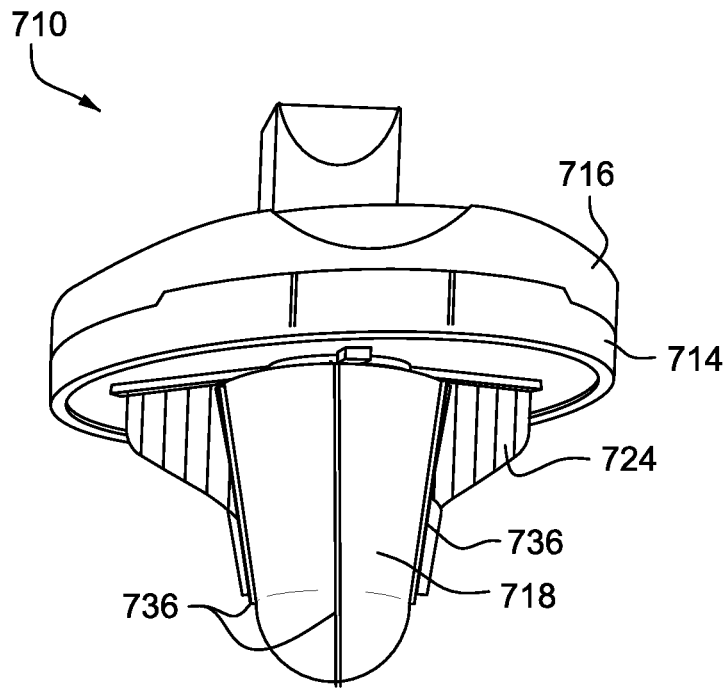
Figure 16B:
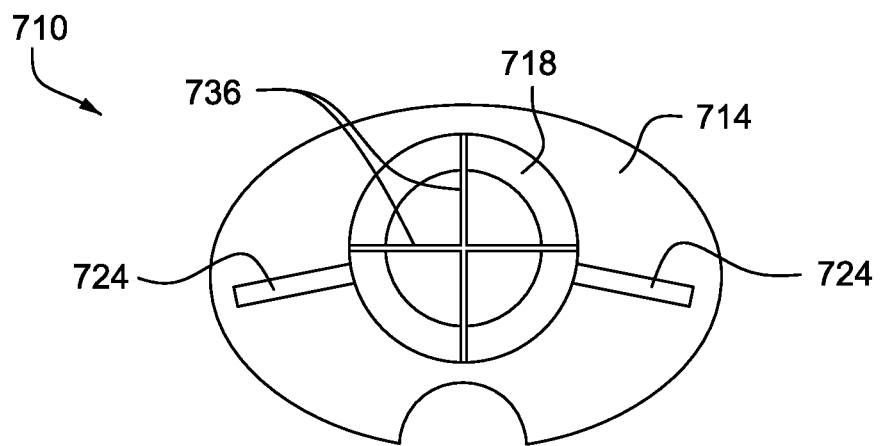
Figure 17A:
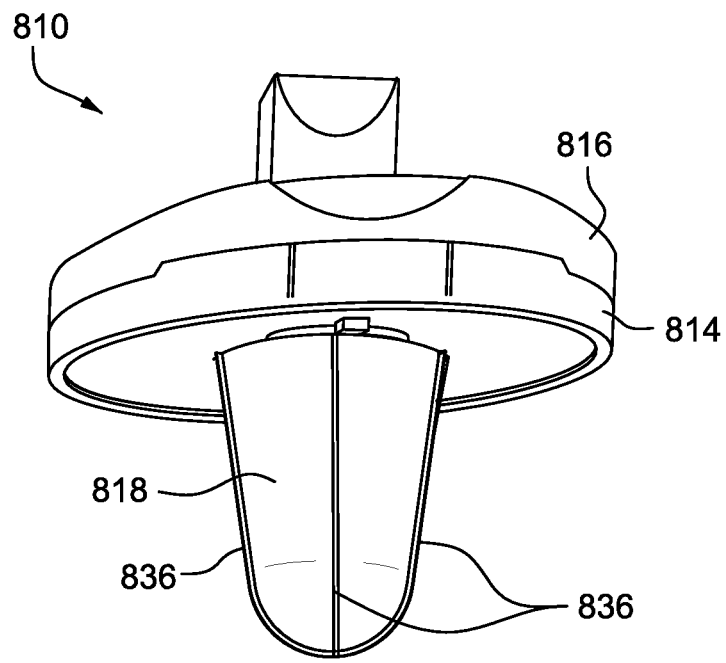
Figure 17B:
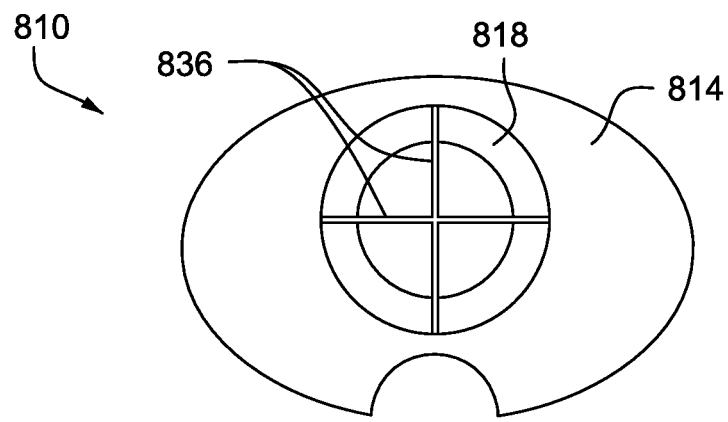
Figure 18A:
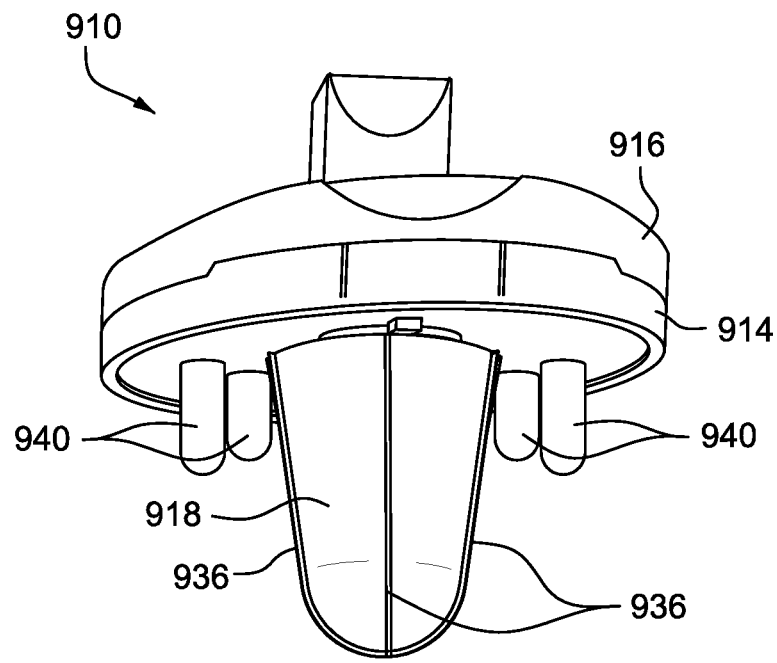
Figure 18B:
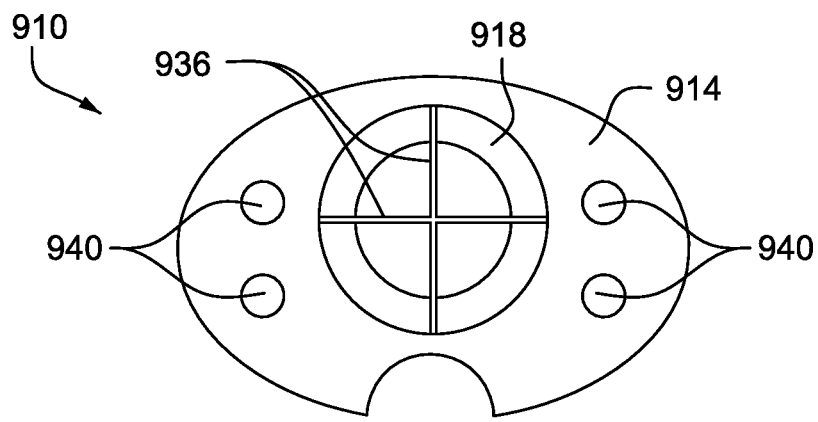

In some situations, the patient's bone canal may have a shape that widely varies from the shape of the stem due to, for example, excessive bone loss. In such situations, the stem might not sufficiently anchor the knee replacement device to the patient's bones. FIGS. 14A-14C illustrate another exemplary stem 518 that may be used when the shape of the bone canal varies widely from the shape of the stem.

The stem 518 is similar to all of the previously disclosed stems. For example, the stem 518 includes a central bore 530, an internal receiving portion 532, an outer surface 534 and at least one projection 536. Although illustrated as being centered, the central bore 530 may be offset. The internal receiving portion 532 may include a seat 538 and gaps 540.

In addition, the stem 518 may include a tapered projection (lobe) 550 mounted to the outer surface 534.

The tapered projection 550 may provide additional surface area for a better fit within the patient's bone canal. The tapered projection 550 may have any shape. For example, the tapered projection 550 may have a partially frusto-conical shape (i.e., the cross-sectional shape of the tapered projection 550 may be an incomplete circle). As illustrated in FIG. 14C, the tapered projection 550 may have a partially conical shape (i.e., the cross-sectional shape of the tapered projection 550 may be an incomplete circle). It should be understood that the cross-sectional shape of the tapered projection is not limited to incomplete circles or rounded shapes.

The tapered projection 550 may be tapered in the same direction as the outer surface 534. That is, the taper of the tapered projection 550 may be in a direction substantially parallel to the longitudinal axis of the stem 18. In addition, the taper of the tapered projection 550 may be the same as or different from the taper of the outer surface 534.

The tapered projection 550 may be made of the same material as the outer surface 534 or any other bio-compatible material. In addition, the surface of the tapered projection 554 may be a mesh or solid material. Furthermore, the tapered projection 550 may be hollow or solid-filled. Also, the surface of the tapered projection 550 may be stiff or flexible.

It is contemplated that the surface of the tapered projection 554 may be roughened, polished or coated to add texture to the tapered projection 554 to provide some rotational support. For example, the tapered projection 554 have a grit blasted finish and/or a coating that includes (but is not limited to) hydroxyapatite or similar elements or any other biocompatible material. The grit blasted finish and/or coating may prevent bony ingrowth (or ongrowth), which may facilitate easy removal of the stem 518. It is further contemplated that instead of a grit blasted finish or in addition to the grit blasted finish, other textured features may be added to the tapered projection 554 to increase the surface roughness of the tapered projection 554.

The tapered projection 550 may be removably or permanently mounted to the outer surface 534 by any means. For example, the tapered projection may be mounted by way of adhesive, chemical bond, or mechanical fastener. It is contemplated that the tapered projection 550 may be formed integrally with the outer surface 534.

FIGS. 14A and 14B show the tapered projection 550 being positioned between neighboring projections 536. It is also contemplated that the tapered projection 550 may straddle on projection 536. It is further contemplated that the tapered projection 550 may extend all of the way between neighboring projections 536 or only part of the way between projections 536. In addition, the tapered projection 550 may extend the entire axial length of the stem 518 or only part of the axial length of the stem 18.

It should be understood that although only one tapered projection 550 is illustrated in FIGS. 14A-14C, the stem 518 may include more than one tapered projection 550. In addition, the tapered projection 550 may be different from the projections 536. For example, the projections 536 may be non-tapered (i.e., the both ends of the projections 536 may project the same distance from the outer surface 534). In addition, the tapered projection may be larger than the projections 536. Also, additional projections 536 may be positioned on the tapered projection 550.

FIGS. 15A-18B illustrate exemplary knee replacement devices that are formed unitarily. The knee replacement device 610 may include a tibial component 614, a bearing insert 616 and a stem 618. The knee replacement device 610 may also (or alternatively) include a femoral component with a stem 618. The stem 618 may include projections 636 and may be hollow and open at the bottom. In addition, the tibial component 614 may include engagement portions 624.

The knee replacement device 710 may be similar to the knee replacement device 610 except that the stem 718 may be closed instead of open at the bottom. Thus, the knee replacement device 710 may include a tibial component 714, a bearing insert 716 and engagement portions 724. It should be understood that the knee replacement device 710 may also (or alternatively) include a femoral component with a stem 718. In addition, the projections 736 may extend all the way around the bottom of the stem 718.

The knee replacement device 810 may be similar to the knee replacement devices 610 and 710 except that the tibial component 814 may lack engagement portions. Thus, the knee replacement device 810 may include a bearing insert 816 and a stem 818. It should be understood that the knee replacement device 810 may also (or alternatively) include a femoral component with a stem 818. In addition, the projections 836 may extend all the way around the bottom of the stem 818.

The knee replacement device 910 may be similar to the knee replacement devices 610, 710 and 810. Thus, the knee replacement device 910 may include a tibial component 914, a bearing insert 916 and a stem 918. It should be understood that the knee replacement device 910 may also (or alternatively) include a femoral component with a stem 918. In addition, the projections 936 may extend all the way around the bottom of the stem 918. Furthermore, the tibial component 914 may include pegs 940 that extend downward away from the tibial component 914.

The pegs 940 may provide additional fixation to the patient's bone including increased rotational and translational stability. The pegs 940 may also contribute to increased implant longevity and durability. The pegs 940 can be made of any biocompatible material and may be configured to promote bony ingrowth. Additionally, the pegs 940 may be configured to facilitate easier removal from the patient's bones. For example, the pegs 940 may be configured to be easily cut or divided (precut). The pegs 940 can vary in shape, size, location, length, material and surface finish. It is contemplated that the pegs 940 may unitarily formed with the tibial component 914 or may be attached to the tibial component 914 by varies means (e.g., chemical bond, adhesive, mechanical fixation, etc.).

It should be understood that in configurations utilizing two stems, one or both stems may be the stem 18. Alternatively, one or both stems may be the stem 118, 218, 318, 418, 518, 618, 718, 818 or 918.

It should be understood that the taper of the outer surface 34 (or 134, 234, 334, 444 or 534) may substantially match the taper of the patient's bone canal when the voids between the bone canal walls and the outer surface 34 (or 134, 234, 334, 444 or 534) are minimized. The tapers do not have to exactly match.

It should be understood that the dimensions of the outer surface 34 (or 134, 234, 334, 444 or 534) may substantially match the dimensions of the patient's bone canal when a difference between the dimensions is within manufacturing tolerances. The dimensions do not have to exactly match.

It should be understood that the shape of the outer surface 34 (or 134, 234, 334, 444, or 534) may substantially match the shape of the bone canal when both are tapered or both are not tapered and the differences in the respective cross-sectional shapes minimize the voids between the bone canal walls and the outer surface 34 (or 134, 234, 334, 444 or 534). The shapes do not have to exactly match.

In addition, it is contemplated that any of the above disclosed stems could be non-modular cone shaped portions permanently attached to the rest of the implant. It is further contemplated that any of the above stems could be formed as one piece with other components of the knee replacement implant or all of the components of the knee replacement implant. In the non-modular, permanently fixed configurations, different knee replacement implants can have different sized cone shaped portions. Such knee replacement implants may be used as routine primary implants for average replacements or as primary and secondary implants for more complicated replacements.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A fixation device for a knee replacement, the fixation device comprising:
   a stem configured to be removably attached to one of a tibial component of the knee replacement and a femoral component of the knee replacement, the stem having a continuously tapered outer surface and having a distal end that is distal to said one of the tibial component and the femoral component; and
   a fixation bolt configured to secure the stem to said one of the tibial component and the femoral component, the fixation bolt being removably attachable to the stem and at least one of the tibial component and the femoral component, the fixation bolt being configured to be received by the stem before being received by the tibial component or the femoral component,
   wherein the stem is configured so that the continuously tapered outer surface engages a patient's bone when the stem is inserted into a bone canal within the patient's bone, and
   wherein the continuously tapered outer surface of the stem at the distal end is configured to mechanically fix the knee replacement to the patient's bone by being wedged within the bone canal.

2. The fixation device of claim 1, wherein the continuously tapered outer surface comprises at least one projection configured to engage the patient's bone when the continuously tapered outer surface is wedged within the patient's bone canal.

3. The fixation device of claim 2, wherein the at least one projection is a plurality of projections.

4. The fixation device of claim 2, wherein the at least one projection extends along a length of the stem.

5. The fixation device of claim 1, wherein the continuously tapered outer surface has a textured finish.

6. A knee replacement device comprising:
   a tibial component configured to be secured to a patient's tibia;
   a femoral component configured to be secured to the patient's femur;
   a bearing insert sandwiched between the tibial component and the femoral component; and
   the fixation device of claim 1.

7. The fixation device of claim 1, further comprising a tapered projection on the continuously tapered outer surface, the tapered projection being tapered in the same direction as the continuously tapered outer surface.

8. The fixation device of claim 7, wherein the continuously tapered outer surface comprises at least one non-tapered projection configured to engage the patient's bone when the continuously tapered outer surface is wedged within the patient's bone canal.

9. The fixation device of claim 8, wherein the tapered projection is positioned between two non-tapered projections.

10. The fixation device of claim 8, wherein the tapered projection straddles the at least one non-tapered projection.

11. The fixation device of claim 7, wherein the tapered projection is hollow.

12. The fixation device of claim 7, wherein the tapered projection is solid-filled.

13. The fixation device of claim 7, wherein the angle of taper for the tapered projection is different from the angle of taper for the continuously tapered outer surface.

14. The fixation device of claim 7, wherein the angle of taper for the tapered projection is the same as the angle of taper for the continuously tapered outer surface.

15. The fixation device of claim 7, wherein the tapered projection has a mesh surface.

16. The fixation device of claim 7, wherein the tapered projection has a solid surface.

17. The fixation device of claim 7, wherein the surface of the tapered projection is flexible.

18. The fixation device of claim 7, wherein the surface of the tapered projection is rigid.

19. A knee replacement device comprising:
a tibial component configured to be secured to a patient's tibia;
a femoral component configured to be secured to the patient's femur;
a bearing insert sandwiched between the tibial component and the femoral component; and
the fixation device of claim 7.

20. A fixation device for a knee replacement with a tibial component configured to be secured to a tibia of a patient and a femoral component configured to be secured to a femur of a patient, the fixation device comprising:
a stem configured to be wedged into one of the patient's bone canal; and
a fixation bolt configured to secure the stem to said one of the tibial component and the femoral component, the fixation bolt being removably attachable to the stem and at least one of the tibial component and the femoral component, the fixation bolt being configured to be received by the stem before being received by the tibial component or the femoral component,
wherein the stem comprises an outer surface and at least a portion of the outer surface is continuously tapered,
wherein the outer surface of the stem is shaped so that a furthest extension of the stem away from the knee replacement wedges in the bone canal when the stem is inserted into the bone canal.

21. The fixation device of claim 20, wherein the outer surface comprises at least one projection configured to resist rotational movement of the stem in the bone canal.

22. The fixation device of claim 20, wherein the stem is integral to the knee replacement.

23. The fixation device of claim 20, wherein the outer surface is textured.

24. The fixation device of claim 20, wherein the outer surface comprises a non-tapered portion.

25. The fixation device of claim 24, wherein both the continuously tapered portion of the outer surface and the non-tapered portion of the outer surface are shaped to be wedged within the bone canal.

26. The fixation device of claim 20, wherein a cross-sectional shape of the stem is asymmetrical.

27. The fixation device of claim 20, wherein a cross-sectional shape of the stem is symmetrical.

28. A knee replacement device comprising:
a tibial component configured to be secured to a patient's tibia;
a femoral component configured to be secured to the patient's femur;
a bearing insert sandwiched between the tibial component and the femoral component; and
the fixation device of claim 20.

29. A knee replacement device comprising:
a tibial component configured to be secured to a patient's tibia;
a femoral component configured to be secured to the patient's femur; and
a bearing insert sandwiched between the tibial component and the femoral component;
a fixation device formed unitarily with one of the tibial component or the femoral component, the fixation device comprising a stem configured to be wedged into the patient's bone canal, the stem comprising an outer surface and at least a portion of the outer surface is continuously tapered; and
a fixation bolt configured to secure the stem to said one of the tibial component and the femoral component, the fixation bolt being removably attachable to the stem and at least one the tibial component and the femoral component, the fixation bolt having a first threaded portion configured to engage a second threaded portion of the tibial component or the femoral component,
wherein the outer surface of the stem is shaped so that a furthest extension of the stem away from the bearing insert wedges in the bone canal when the stem is inserted into the bone canal.

30. The knee replacement device of claim 29, wherein the stem is open at an end that is distal to the tibial or femoral component.

31. The knee replacement device of claim 29, wherein the stem is closed at an end that is distal to the tibial or femoral component.

32. The knee replacement device of claim 29, further comprising a plurality of pegs extending from the tibial component or the femoral component, the plurality of pegs being configured to secure the knee replacement device to a user's bone.

33. The knee replacement device of claim 29, further comprising a tapered projection on the stem.

34. The knee replacement device of claim 33, wherein the continuously tapered outer surface of the stem at the distal end of the stem and the tapered projection are configured to mechanically fix the knee replacement to the patient's bone by being wedged within the bone canal.

35. The knee replacement device of claim 34, wherein the tapered projection is formed unitarily with the stem.

36. A fixation device for a knee replacement prosthesis with a tibial component and a femoral component, the fixation device comprising:
a tapered stem configured to be attached to one of the tibial component and the femoral component;
at least one projection on an outer surface of the tapered stem, the at least one projection being configured to resist a rotational movement of the tapered stem when the tapered stem is inserted into a patient's bone canal; and a fixation bolt configured to secure the tapered stem to the tibial component or the femoral component, the fixation bolt being removably attachable to the stem and at least one of the tibial component and the femoral component, the fixation bolt having a first threaded portion configured to engage a second threaded portion of the tibial component or the femoral component, wherein the tapered stem comprises a continuously tapered outer surface configured to be wedged within the patient's bone canal.

37. The fixation device of claim 36, wherein the outer surface comprises a non-tapered portion.

38. The fixation device of claim 37, wherein both the continuously tapered portion of the outer surface and the non-tapered portion of the outer surface are shaped to be wedged within the patient's bone canal.

* * * * *